United States Patent
Uhr et al.

(10) Patent No.: US 9,222,253 B2
(45) Date of Patent: Dec. 29, 2015

(54) MIXTURES OF POLYMERS CONTAINING BLOWING AGENT, INSECTICIDES, AND WAXES

(75) Inventors: Hermann Uhr, Leverkusen (DE); Cyndi Fink, Coraopolis, PA (US); Navnit Bhuleshwar Upadhyay, Presto, PA (US)

(73) Assignees: LANXESS DEUTSCHLAND GMBH, Cologne (DE); LANXESS Corporation, Pittsburgh, PA (US)

( * ) Notice: Subject to any disclaimer, the term of this patent is extended or adjusted under 35 U.S.C. 154(b) by 107 days.

(21) Appl. No.: 14/127,043

(22) PCT Filed: Jun. 21, 2012

(86) PCT No.: PCT/EP2012/062002
§ 371 (c)(1),
(2), (4) Date: Mar. 6, 2014

(87) PCT Pub. No.: WO2012/175628
PCT Pub. Date: Dec. 27, 2012

(65) Prior Publication Data
US 2014/0206785 A1    Jul. 24, 2014

Related U.S. Application Data

(60) Provisional application No. 61/499,317, filed on Jun. 21, 2011.

(30) Foreign Application Priority Data

Oct. 11, 2011 (EP) .................... 11184694

(51) Int. Cl.
| | | |
|---|---|---|
| A01N 25/16 | (2006.01) | |
| A01N 25/26 | (2006.01) | |
| A01N 37/00 | (2006.01) | |
| E04B 1/72 | (2006.01) | |
| A01N 25/24 | (2006.01) | |
| A01N 25/34 | (2006.01) | |
| A01N 51/00 | (2006.01) | |
| A01N 37/46 | (2006.01) | |

(52) U.S. Cl.
CPC . *E04B 1/72* (2013.01); *A01N 25/16* (2013.01); *A01N 25/24* (2013.01); *A01N 25/34* (2013.01); *A01N 37/46* (2013.01); *A01N 51/00* (2013.01)

(58) Field of Classification Search
None
See application file for complete search history.

(56) References Cited

U.S. PATENT DOCUMENTS

| | | |
|---|---|---|
| 5,385,951 A | 1/1995 | Soderberg |
| 5,985,943 A | 11/1999 | Hahn et al. |
| 6,033,731 A | 3/2000 | Liebert et al. |
| 6,080,796 A | 6/2000 | Liebert et al. |
| 6,221,375 B1 | 4/2001 | Howse |
| 6,228,902 B1 | 5/2001 | Brueggeman et al. |
| 2008/0096991 A1 | 4/2008 | Upadhyay et al. |
| 2010/0016468 A1 | 1/2010 | Bergstrom |
| 2010/0307101 A1* | 12/2010 | Ishaque et al. ............... 52/741.3 |
| 2011/0201662 A1 | 8/2011 | Ishaque et al. |

FOREIGN PATENT DOCUMENTS

| | | | |
|---|---|---|---|
| JP | 63152648 A | 6/1988 | |
| JP | 63159451 A | 7/1988 | |
| JP | 63254143 A | 10/1988 | |
| JP | 10036549 A | 2/1998 | |
| WO | 2009080464 A2 | 7/2009 | |
| WO | WO 2009080723 A1 * | 7/2009 | ............... C08J 9/224 |

OTHER PUBLICATIONS

Wei et al., "Montan Wax: The state-of-the-art review," (2014) Journal of Chemical and Pharmaceutical Research. 6(6): 1230-1236.*
Database WPI, Week 200947, Thomson Scientific, London, GB, XP002670122, Jul. 9, 2009, AN2009-L30667, 2 pages.
Database WPI, Week 198848, Thomson Scientific, London, GB, XP002670124, Oct. 20, 1988, AN1988-341922, 2 pages.
Database WPI, Week 199816, Thomson Scientific, London, GB, XP002670125, Feb. 10, 1998, AN1998-175034, 1 page.
International Search Report from International Application PCT/EP2012/062002, Sep. 14, 2012, 3 pages.

* cited by examiner

*Primary Examiner* — Kara Boyle

(57) ABSTRACT

The present invention relates to mixtures of blowing agent-containing polymers, wax and insecticides, to coated polymer particles, to methods for producing coated polymer particles, to the use of these particles and mixtures in the production of polymer foams, to the use thereof for protecting polymer foams against infestation by insects, principally termites, and also to materials of construction and building materials produced from the insecticide-containing polymer foams.

18 Claims, No Drawings

MIXTURES OF POLYMERS CONTAINING BLOWING AGENT, INSECTICIDES, AND WAXES

The present invention relates to mixtures of blowing agent-containing polymers, wax and insecticides, to coated polymer particles, to methods for producing coated polymer particles, to the use of these particles and mixtures in the production of polymer foams, to the use thereof for protecting polymer foams against infestation by insects, principally termites, and also to materials of construction and building materials produced from the insecticide-containing polymer foams.

Polymer foams are being used increasingly in the building industry on account of their outstanding processing and insulating properties. In certain regions and certain climatic zones, these foams, or building materials produced therefrom, are infested by animal pests, especially termites. Termites in particular may cause damage to the substance of these foams and building materials, by feeding, to such an extent that the insulating effect and mechanical stability of the moldings produced from the foams is restricted. Oftentimes, therefore, statutory provisions prescribe insecticidal protection of shaped components to be installed in preferred habitats of termites.

It is already long-established art to protect polystyrene foams or foams of other polymers, and construction materials produced from them, against infestation, especially by termites, through the use of compounds that are toxic toward insects. Moreover, variously methods are in existence for the production of insecticide-containing polymer foams, more particularly of insecticide-containing EPS (expanded polystyrene) foams.

Thus, for example, U.S. Pat. No. 6,033,731 A and JP 63152648 A disclose methods for incorporating insecticides into the blowing agent-containing EPS particles. Another method for producing insecticide containing polymer foams, in which the insecticides are incorporated into the polymer melt first of all, prior to foaming, is known from WO 2010/046379. U.S. Pat. No. 6,080,796 B discloses a method for producing insecticide-containing polymer foams where the insecticides are first mixed with the monomers, more particularly with styrene, and then polymerized to form EPS granules, and foamed.

A disadvantage of the methods above is that only when comparatively high quantities of insecticides are used is it possible to apply a sufficiently effective quantity to the surface of the polymer particles to be foamed, and that, as a result, process-water loadings are produced that necessitate the deployment of further purification processes. These methods, therefore, are unsuitable for use in industrial operations, for economic and environmental reasons.

Other methods for producing insecticide-containing polymer foams, by impregnating the polymer particles with an insecticide prior to foaming, are known from JP 63159451 A, US 2010/0016468 A and US 2008/0096991 A. A disadvantage of these methods is that the insecticide-containing layers have only limited durability and are sensitive to processing.

Moreover, methods for producing insecticide-containing polymer foams by coating an EPS particle with a mixture of an insecticide and a resin as adhesive are known from JP 10036549 A and JP 63254143 A. A further method for producing insecticide-containing polymer foams, in which EPS particles are coated with a mixture of glycerol esters and hinders, is known from WO 2009/080723. A disadvantage of these aforementioned methods is that the coated EPS particles tend to agglomerate and are therefore not suitable for producing all shaped components from polymer foams. Furthermore, the insecticide/adhesive mixture has to be sprayed in order to be able to ensure uniform distribution on the surface of the polymer particles, and this leads to further technical effort and complexity for the user. This method, therefore, cannot be employed efficiently in industrial operations.

The object, therefore, was to provide a method for producing insecticide-containing polymer foams that allows the disadvantages of the prior art to be overcome and that is able to produce polymer foams efficiently and using reduced quantities of insecticides.

It has now surprisingly been found that through use of the mixtures according to the invention it is possible to produce insecticide-containing polymer foams and coated polymer particles featuring highly active protection and to do so efficiently in industrial operations.

The invention accordingly provides mixtures comprising at least one blowing agent-containing polymer, at least one insecticide, and at least one wax.

The blowing agent-containing polymers constitute polymer particles in which the blowing agents can be released by heating and which contain these agents in dissolved or encapsulated form.

Blowing agents in the sense of the invention may be inorganic, organic, or reactive. Inorganic blowing agents include carbon dioxide, nitrogen, water, helium, air, or argon.

The organic blowing agents are aliphatic hydrocarbons having 1 to 9 carbon atoms, and partially or per-halogenated aliphatic hydrocarbons having 1 to 4 carbon atoms. The aliphatic hydrocarbons are preferably methane, ethane, propane, n-butane, isobutene, n-pentane, isopentane, and neopentane. The fully and partially halogenated aliphatic hydrocarbons are fluorocarbon compounds, chlorocarbon compounds and chlorofluorocarbon compounds. Fluorocarbon compound halogenated blowing agents employed are preferably methyl fluoride, perfluoromethane, ethyl fluoride, difluoromethane, 1,1-difluoroethane, 1,1,1-fluoroethane, 1,1,1,2-tetrafluoroethane, pentafluoroethane, difluoromethane, perfluoroethane, 2,2-difluoro-propane, 1,1,1-trifluoropropane, perfluoropropane, difluoropropane, difluoropropane, perfluoro-butane, or perflourocyclopentane. The partly halogenated chlorocarbon compounds and chlorofluorocarbon compounds are preferably methyl chloride, methylene chloride, ethyl chloride, 1,1,1-trichloroethane, chlorodifluoromethane, 1,1-dichloro-1-fluoroethane, 1-chloro-1,1-difluoroethane, 1,1-dichloro-2,2,2-trifluoroethane, and 1-chloro-1,2,2,2-tetrafluoroethane. The fully halogenated chlorofluorocarhon compounds are preferably trichloromonofluoromethane, dichlorodifluoromethane, trichlorotrifluoroethane, 1,1,1-trifluoroethane, pentafluoroethane, dichlorotetrafluoroethane, chloroheptafluoropropane, and dichlorohexafluoropropane.

Chemically reactive blowing agents are substances which off gases under thermal exposure. These are preferably azodicarboxylic diamide, azodiisobutyronitrile, benzenesulfonyl hydrazide, 4,4-oxybenzenesulfonyl semicarbazide, p-toluenesulfonyl semicarbazide, barium azodicarboxylate, N,N'-dimethyl-N,N'-dinitrosotherephthalamide, and trihydrazinotriazine.

Another preferred blowing agent mixture comprises 0 to 100 wt % of carbon dioxide, 0 to 50 wt % of water and 0 to 75 wt % of an alcohol, as for example methanol or ethanol, or of a ketone or ether.

Polymers which can be used are all polymers that can be foamed by means of blowing agents, such as, for example, polypropylene, polyethylene, polyesters, such as more particularly polyethylene terephthalate, polyurethane, or polystyrene. Preferred polymers used are polystyrenes. In the sense of the invention, polystyrene (PS) is used as a collective term for homopolymers and copolymers of styrene, other vinylaromatic monomers, and optionally further comonomers. PS comprehends, for example, standard polystyrene (General Purpose Polystyrene, GPPS), high impact polystyrene (HIPS, containing polybutadiene rubber or polyisoprene rubber, for example), styrene-maleic acid (anhydride) polymers, acrylonitrile-butadiene-styrene polymers (ABS), styrene-acrylonitrile polymers (SAN), α-methylstyrene-acrylonitrile polymer (AMSAN), or mixtures thereof (component K1). Preferred PS is standard polystyrene, i.e., a polystyrene having a molar styrene monomer fraction of at least 95%. Additionally preferred PS is α-methylstyrene-acrylonitrile polymer (AMSAN).

Furthermore, PS also encompasses blends of one or more of the aforementioned polymers (component K1) with one or more thermoplastic polymers (component K2) such as, for example, polyphenylene ethers (PPE), polyamides (PA), polyolefins, such as polypropylene (PP) or polyethylene (PE), polyacrylates, such as polymethyl methacrylate (PMMA), polycarbonates (PC), polyesters, such as polyethylene terephthalate (PET) or polybutylene terephthalate (PBT), polyethersulfones (PES), polyether ketones (PEK), or polyethersulfides (PES).

The blowing-agent polymers may be produced by methods known to the skilled person, such as, for example, by a) suspension polymerization of a monomer, e.g., styrene, in the presence of blowing agents, to produce blowing agent-containing, polymer particles directly; b) impregnation of blowing agent-free polymer particles with the blowing agent under pressure in a heated suspension, with the blowing agent diffusing into the softened particles (on cooling of the suspension under pressure, blowing agent: containing polymer particles are obtained); or c) mixing of the blowing agent into a polymer melt by means of an extruder or other mixing apparatus (the blowing agent-containing melt is discharged under pressure and pelletized to form polymer particles by means of underwater pressure pelletization, for example). This method is especially suitable for producing blowing agent-containing polystyrene particles (EPS particles).

Besides the blowing agent, the blowing agent-containing polymers may additionally comprise further adjuvants such as, for example, dyes, binders, antistats, hydrophobizing agents, inorganic fillers, such as silica, for example, and flame retardants.

Furthermore, the mixtures according to the invention may also comprise further adjuvants such as, for example, dyes, hinders, antistats, hydrophobizing agents. inorganic fillers, such as silica, for example, and flame retardants.

It has emerged, moreover, that particularly when using adjuvants consisting of esters of trihydric alcohols and long-chain fatty acids, more particularly in the presence of glycerol esters, it is not possible to employ the mixtures according to the invention. The use of glycerol esters as adjuvant is therefore excluded from the invention.

The insecticides may in principle be any insecticides which in terms of their activity spectrum are capable of preventing infestation by insects, more particularly termites.

The structures associated in each case with the common name can be found at the following link: http://www.alanwood.net/pesticides/index.html With particular preference the insecticides which can be employed are as follows:

nicotine receptor agonists/antagonists, such as clothianidin, dinotefuran, imidadacloprid, imidaclothiz, thiamethoxam, thiacloprid, nintenpyram, nithiazine, acetamiprid or paichongding;

pyrazoles and phenylpyrazoles such as chlorantraniliprole, cyantraniliprole, dimetilan, isolan, tebufenpyrad, tolfenpyrad, acetoprole, ethiprole, fipronil, flufiprole, pyraclofos, pyrafluprole, pyriprole, hydramethylnon;

growth regulators from the classes of chitin synthesis inhibitors, such as benzoylureas: histrifluron, chlorbenzuron, chlorfluazuron, dichlorbenzuron, diflubenzuron, flucofuron, flucycloxuron, flufenoxuron, hexaflumuron, lufenuron, novaluron, noviflumuron, penfluron, sulcofuron, teflubenzuron or triflumuron; buprofezin, diofenolan, hexythiazox, etoxazole, chlfentazine; ecdysone antagonists and antagonists such as chromafenozide, furan tebufenozide halofenozide, methoxyfenozide, tebufenozide, yishijing, azadirachtin; juvenoids such as dayoutong, epofenonane, fenoxycarb, hydroprene, kinoprene, methoprene, pyriproxyfen, triprene; lipid biosynthesis inhibitors such as spirodiclofen, spiromesifen, spirotetramat;

organo(thio)phosphates such as acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isofenphos, isoxathion, malathion, methamidophos, methidathion, methylparathion, mevinphos, monocrotophos, oxydemetonmethyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates such as alanycarb, aldicarb, bendiocarb, benfuracarb, carbaryl, carbofuran, carbosulfan, fenoxycarb, furathiocarb, methiocarb, methomyl, oxamyl, phenoxycarb, pirimicarb, pyrethroids such as allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cybalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, imiprothrin, phenothrin, empenthrin, esbiothrin;

GABA antagonists such as endosulfan, pyrafluprole, pyriprole;

macrocyclic lactone insecticides such as abarmectin, emamectin, milbemectin, lepimectin, spinosad;

site I electron transport inhibitors such as fenazaquin, fenpyroximate pyrimidifen, pyridaben, tebufenpyrad, tolfenpyrad, flufenerim, hydramethylnon, dicofol;

site-II and site III electron transport inhibitors such as acequinocyl, fluacyprim, rotenone;

oxidative phosphorylation inhibitor compounds or decouplers, such as cyhexatin, diafenthiuron, fenbutatin oxide, tralopyril, chlorphenapyr, propargite;

inhibitors of chitin biosynthesis such as cyromazine;

oxidase inhibitors, such as piperonyl butoxide (PBO);

sodium channel modulators, such as indoxacarb, metaflumizone;

other active ingredients, such as amidoflumet, benclothiaz, bifenazate, borate, cartap, chlorantraniliprole, flonicamid, pyridalyl, pymetrozine, thiocyclam, flubendiamide, cyenopyrafen, cyflumetofen, flupyrazofos;

With very particular preference the insecticides are:

thiametoxam, nintenpyram, thiacloprid, imidacloprid, fipronil, chlorphenapyr, hydramethylnon, flufenoxuron, triflumuron, phenoxycarb, tralopyril, cyfluthrin, deltamethrin, permethrin, transfluthrin, diflubenzuron, azamethiphos, dichlorvos, bendiocarb, phenoxycarb, cyhalothrin, cyphenothrin, cypermethrin, prallethrin, tetramethrin, phenothrin, empenthrin, esbiothrin, abamectin, cyromazine, pyriproxyfen, esfenvalerate.

It is also possible in each case to use mixtures of the insecticides, in which case synergistic effects are frequently also observed.

Even more preferred for use as insecticides are thiametoxam, thiachloprid and imidachloprid. It is likewise possible to employ these selected insecticides in mixtures with other insecticides from those given above. Synergistic effects are frequently observed for these mixtures.

The moldings of the invention and construction materials produced from them are protected from infestation with insects. The insects in question are, in particular, biting insects such as cockroaches (e.g., *Blatella germanica, Periplaneta americana, Blatta orientalis, Supella longipalpa*), beetles, such as, for example. *Sitiophilus granarius, Tenebrio molitor, Dermestes lardarius, Stegobium paniceum, Anobium punctatum, Hylotrupes bajulus*), termites such as, for example, *Reticulitermes lucifugus, Reticulitermes flavipes, Reticulitermes virginicus, Reticulitermes hageni*), ants, such as *Lasius niger, Monomorium pharaonis*, and wasps such as, for example *Vespula germanica*.

Especially preferred is protection against all customary termite species, such as, for example, *Reticulitermes lucifugus, Reticulitermes flavipes, Reticulitermes virginicus, Reticulitermes hageni*, and also the termite species belonging to the genera *Coptotermes* and *Mastotermes*.

In order to provide the blowing agent-containing polymers and construction materials or moldings produced from them with protection, additionally, from infestation by molds, the mixtures according to the invention may also further comprise fungicides. In general it is possible to employ any fungicides which have an activity with respect to the molds.

With very particular preference the fungicides in question are azaconazole, bromuconazole, cyproconazole, dichlobutrazole, diniconazole, hexaconazole, metaconazole, penconazole, propiconazole, tebuconazole, azoxystrobin, fludioxonil, dichlofluanid, tolylfluanid, fluorfolpet, methfuroxam, carboxin, fenpiclonil, butenafin, imazalil, N-octylisothiazolin-3-one, dichloro-N-octylisothiazolinone, mercaptobenzothiazole, thiocyanatomethylthiobenzothiazole, thiabendazole, N-butylbenzisothiazolinone, 1-hydroxy-2-pyridinethione (and the Cu, Na, Fe, Mn, and Zn salts thereof), tetrachloro-4-methylsulfonylpyridine, 3-iodo-2-propynyl n-butylcarbamate, bethoxazin, 2,4,5,6-tetrachloroisophthalodinitrile, and carbendazim.

To enhance the activity it is also possible in each case, optionally, to use mixtures of two or more of the fungicides.

If a fungicide is additionally used, then the blowing agent-containing polymers, more particularly the polystyrenes, or the construction materials or moldings produced from them are additionally provided with further protection with respect to molds and basidiomycetes.

Mention may made, for example, of microorganisms of the following genus:

*Alternaria*, such as *Alternaria tenuis,*
*Aspergillus*, such as *Aspergillus niger,*
*Chaetomium*, such as *Chaetomium globosum,*
*Coniophora*, such as *Coniophora puetana,*
*Lentinus*, such as *Lentinus tigrinus,*
*Penicillium*, such as *Penicillium glaucum,*
*Polyporus*, such as *Polyporus versicolor,*
*Aureobasidium*, such as *Aureobasidium pullulans,*
*Sclerophoma*, such as *Sclerophoma pityophila,*
*Trichoderma*, such as *Trichoderma viride.*

The waxes for the purposes of the invention may be all natural, chemically modified or unmodified, and synthetic waxes.

Generally speaking, the waxes are not pure substances, but instead are in some cases highly complex mixtures of different homologs, and also structures different in their type.

Preference is given to natural waxes, such as cotton wax, carnauba wax, candelilla wax, esparto wax, guaruma wax, japan wax, china wax, cork wax, montan wax, paraffin waxes, bayberry wax, ouricury wax, sugarcane wax, castor wax, soya wax, beeswax, uropygial gland oil, wool wax, shellac wax, spermaceti, microwaxes, ceresin or ozokerite. The chemically modified waxes used are hard waxes such as hydrogenated jojoba waxes, montan waxes, and Sasol waxes. Synthetic waxes come preferably from the group of the polyalkylene waxes, such as polyolefin waxes, polyethylene waxes, Fischer-Tropsch waxes, polypropylene waxes, or from the groups of the polyethylene glycol waxes (carbowaxes) and amide waxes. Suitable polyethylene glycols in the sense of the invention are, in particular, polyethylene glycols having a molar mass of between 6000 and 60 000 g/mol. Particular preference is given using polyethylene waxes, montan waxes, paraffin wax or polyethylene glycol waxes. Especially preferred is the use of paraffin wax of CAS No. 8002-74-2.

To achieve the desired properties it is also possible to use mixtures of the waxes.

A feature of the waxes which can be employed is that they preferably have a melting temperature of 65° C. to 150° C., the waxes more preferably having a melting point of 80° C. to 140° C., and the waxes very preferably have a melting point of 85° C. to 120° C. With further preference the waxes have a melting point of 100° C. to 120° C.

In the solid state the waxes are preferably as hard as possible and, where possible, brittle as well; in the liquid state, their viscosity is preferably to be low.

The mixtures may comprise, for example, 30% to 99% of blowing agent-containing polymer, 0.001% to 0.3% of insecticide, and 0.1% to 30% of wax. The mixtures preferably comprise at least 50% of blowing agent-containing polymer, at least 0.001% to 0.1% of insecticide, and at least 0.001% to 0.5% of wax.

Particularly preferred mixtures are those comprising at least one blowing agent-containing polymer from the series of the polystyrenes, at least one insecticide, and at least one wax having a melting temperature of 65° C. to 130° C. Especially preferred are mixtures which comprise at least one blowing agent-containing polymer from the series of the polystyrenes, at least one insecticide, and at least one wax having a melting temperature of 75° C. to 130° C.

The scope of the invention encompasses all of the parameters and elucidations above and below, including general parameters and elucidations or those specified in preference ranges, and encompasses them with one another, in other words including any desired combination of the respective ranges and preference ranges.

Likewise encompassed by the invention is a method for producing a polymer particle coated with an insecticide-containing layer, in which a mixture of at least one blowing agent-containing polymer and at least one insecticide and at least one wax is foamed at least at a temperature at which the wax melts. These blowing agent-containing polymer particles coated with the insecticide-containing layer are referred to in accordance with the invention as coated polymer particles.

In accordance with the invention, either mixtures of insecticides and waxes are used and are mixed with the blowing agent-containing polymer, or the insecticides are first incorporated into the wax, distributed uniformly, and then mixed with the blowing agent-containing polymer. It is likewise possible, however, for a mixture of insecticides and waxes to be introduced to start with, and for the blowing agent-containing polymers then to be added to this mixture. It is preferred for the blowing agent-containing polymers to be introduced to start with and for the mixtures of insecticides and waxes to be added. After that the mixtures can then be foamed jointly by heating.

The mixtures of the waxes and the insecticides are obtained by mixing the active ingredient with a wax powder in accordance with the customary technical methods, allowing uniform distribution of the substances to be mixed. Examples here include double screw mixers, batch mixers, drum mixers, paddle mixers, screw belt mixers or else fluidized-bed mixers.

For the incorporation of the insecticides and optionally fungicides into the waxes it is possible in principle to use all methods which allow incorporation. In this context, for example, it is possible for the wax to be melted, for the active ingredients to be incorporated into the liquid wax, by stirring, for example, and then for the wax to be allowed to solidify again. In this way the liquid wax can be pressed through dies and so converted to a fine powder or pellets. It is also possible to generate relatively large wax particles, on a flaking belt, for example, and then to comminute them mechanically to the desired size. One effective method of thorough mixing is that of extrusion. From a technical standpoint, this is done using extruders, usually designed as screw extruders, although they may also be ram extruders. The screw extruders may be equipped either with only one shaft or with a twin shaft. They are charged with the mixture of wax and insecticide, and optionally fungicide, by means, for example, of a filling hopper or other feed device. While the screw transports the mixture of solids through the extruder, this mixture is initially warmed and then substantially homogenized and plastified in the screw, at the desired temperature. The extrudate is subsequently pressed via a die from the extruder, in the form, for example, of a strand. Extrusion may be carried out using either single-screw of multiple-screw extruders.

After the extruder, the extrudate is pressed through dies and is generally pelletized into pieces with approximately the same size.

The quantitative ratio of insecticide to wax can generally be selected arbitrarily and is dependent on the amount of the blowing agent-containing polymer used, and also on the amount of wax used.

Generally speaking the proportion of insecticide to wax is between 1:99 to 80:20. Insecticide and wax are used preferably in a quantitative ratio of 5:95 to 70:30 and very preferably in a quantitative ratio of 10:90 to 50:50.

In the application, the amount of insecticide, based on the blowing agent-containing polymer used, may likewise be varied within a very broad range. As well as regional peculiarities in terms of insect population, a key part is also played by the pressure of infestation, and by the insecticidal activity of the active ingredient. With certain active ingredients, such as the nicotinergic agonists and antagonists, for example, repellent effects also have a part to play, and, if this effect is sufficient, the amounts of active ingredient employed may be significantly reduced still further.

Generally speaking, the mixture of wax and insecticide, or insecticide in wax, is employed in an amount such that, based on the blowing agent-containing polymer, there are 10 to 3000 ppm of active ingredient in the mixture. In the mixture there is preferably 20 to 1500 ppm and very preferably 40 to 1000 ppm, based on the blowing agent-containing polymer. The particular figure, however, is heavily dependent on the activity and must be determined by means of experiments.

In accordance with the invention the waxes and the insecticides or other adjuvants may be added at different points in the production operation of the coated polymer particles. It is important, however, that they are added before or during the expansion of the blowing agent-containing polymer, in order to ensure that during this operation the wax melts or at least softens and therefore becomes more adhesive. Generally speaking, this can be accomplished by mixing the waxes with the insecticides and the blowing agent-containing polymers and then foaming the mixture by raising the temperature. The temperature may be raised, for example, by heating using a heating assembly, microwave or by supply of superheated gases. The mixture of blowing agent-containing polymer, waxes, and insecticides is preferably foamed with the aid of superheated steam. This process may be interrupted, for example, by cooling, it being possible by this means to produce preexpanded, coated polymer particles with different particle sizes. The waxes and/or the insecticides may also be admixed in the supply container for the blowing agent-containing polymer, or metered in by special metering units ahead of the expansion. They may also be mixed with the further adjuvants typically employed, such as dyes, for example, and likewise metered in prior to expansion. The coated polymer particles can then be foamed by the user, for example, to polymer foam moldings, or foamed directly further to form components and shaped parts. The waxes and the insecticides may be mixed with the blowing agent-containing polymers or else with the preexpanded, blowing agent-containing polymers. It is likewise possible as well, however, for the preexpanded or prefoamed polymers, containing blowing agent and already coated with the insecticides and waxes of the invention, to be mixed again with the waxes and insecticides and foamed, so producing doubly coated polymer particles.

In one preferred operation the EPS pellets are metered together with a mixture of wax and insecticide. The mixture of wax and insecticide may be homogenized beforehand, for example, by the use of suitable mixers, such as a paddle wheel mixer, for example. The mixture is preferably homogenized and then introduced into the pre-expander. The charging of the pre-expander is carried out preferably with accompanying stirring, using a paddle blade stirrer, for example. Preliminary expansion is carried out preferably using steam. The steam preferably has a temperature of 80° C.-130° C., more preferably 100° C.-115° C., and very preferably 100° C.-105° C. The density of the initial foam here is 300%-100%, preferably 200%-100% and very preferably 150%-100% of the density of the EPS molding.

After expansion has taken place, the coated polymer particles feature a very uniform distribution of wax and insecticide and/or additionally fungicide on the surface.

Likewise encompassed by the invention are the coated polymer particles which are produced in the expansion of the mixtures comprising at least one blowing agent-containing polymer, at least one insecticide, and at least one wax.

In order to be able to ascertain a uniform distribution, dyes may optionally also be added to the wax/insecticide mixtures and waxes, these dyes making subsequent distribution visible. Besides dyes which are visible without auxiliary means, it is also possible for specific fluorescent dyes to be used which allow a distribution of the wax and/or active ingredient to be seen, without visibly surface-coloring the coated polymer particles.

Particularly preferred are coated polymer particles which as the polymer particle to be coated comprise at least one blowing agent-containing polymer from the group of the polystyrenes and for which at least one wax having a melting temperature of 65° C. to 130° C. has been used in the coating. Especially preferred coated polymer particles which as the polymer particle for coating comprise at least one blowing agent-containing polymer from the group of the polystyrenes, and for which at least one wax having a melting temperature of 75° C. to 130° C. has been used for the coating. A blowing agent-containing polymer from the group of the polystyrenes is also referred to as EPS (expanded polystyrene) particles.

Also encompassed by the invention is the use of the coated polymer particles for producing polymer foams and shaped components. Further embraced by the invention are shaped components produced from the mixtures according to the invention or from the coated polymer particles of the invention. Moreover, the structural components produced from the shaped components are likewise encompassed by the invention.

Moldings can be produced from the coated polymer particles by known methods familiar to the skilled person, such as expanding and compression molding. These moldings are insulating panels, etc. The insulating panels may also be composite systems with further materials of construction, such as wood, woodbase materials, or plastics for the purpose of achieving better mechanical stability.

A feature of the moldings or insulating panels is that they are outstandingly protected against feeding by insects, especially termites. At the same time they also constitute a harrier which prevents the insects penetrating the buildings. The moldings and insulating panels may be installed both above and below ground. Moldings produced from the coated polymer particles can be used below ground even in relatively moist environments, without the active ingredient being rapidly washed out into the soil. The invention therefore likewise encompasses the use of the mixture according to the invention or of the coated polymer particles of the invention for protecting polymer foams against insects, more particularly against termites.

A feature of the coated polymer particles is that the wax and the insecticide and optionally additional fungicides are distributed uniformly over the surface. Moreover, the coat is so firmly attached to the surface that in the course of storage, transfer, and processing of the coated polymer particles, the coat remains adhering, but when compression molding is carried out there are no observable changes at all in the properties. In addition, there is no dust burden on the processor, of the kind that constitutes a problem frequently when using the pure insecticides in powder form. It has surprisingly been found, furthermore, that the process-water loadings when producing the EPS particles could be reduced and that, as a result, costs for further cleaning/purification steps are removed, with consequent environmental advantages as well for the EPS particles.

A further advantage of the invention is the protection of the active ingredient or ingredients against influences which lead to degradation of the active ingredients.

EXAMPLES

Example 1

10 g of imidacloprid (Preventol TM) and 40 g of Luwax AF 29 micropowder (BASF, polyethylene wax, m.p. 110-118° C.). are weighed out into a mixing vessel (Kinematica MB 550, laboratory mixer with beater blade) and mixed 2× for 30 sec at medium speed (8000 rpm). This gives a pale yellow, fine, and homogeneous powder. To ascertain the homogeneity, 3 samples were taken and analyzed by HPLC:

| Sample 1 | 19.6% |
| Sample 2 | 19.9% |
| Sample 3 | 19.8% |

Example 2

35 g of Luwax AF 29 (BASF, polyethylene wax, m.p. 110-118° C.) and 15 g of imidacloprid (Preventol TM) are melted at 140° C. with stirring. This gives a viscous, clear, golden yellow melt.

The hot melt at 140° C. is poured onto an aluminum foil and the melt is allowed to cool.

A caramel-colored solid is obtained.

The material is then cooled with dry ice and coarsely ground (Kinematica MB 550, laboratory mixer with beater blade, 8000 rpm): yield: 46.93 g:

To ascertain the homogeneity, samples were taken from 3 sites and the imidacloprid content was determined by means of HPLC:

| Sample 1 | 30.4% |
| Sample 2 | 30.1% |
| Sample 3 | 30.4% |

The particles had a size of approximately 100-300 μm (measured by microscopy).

Example 3

35 g of Luwax Al 3 powder (BASF, homopolymeric polyethylene wax, m.p. 102-108° C.) are melted at 140° C. This gives a viscous, clear, colorless melt. Added to this melt with stirring over the course of 30 minutes, in portions, are 15 g of imidacloprid (Preventol TM).

The hot, golden yellow melt at 140° C. is poured onto an aluminum foil and allowed to cool.

The caramel-colored solid. Is coarsely comminuted, cooled with dry ice, and coarsely ground (Kinematica MB 550, laboratory mixer with beater blade, 8000 rpm).

Particles measured under the microscope 100-300 μm

Yield: 41.22 g

To ascertain the homogeneity, samples were taken from 3 sites and the imidacloprid content was determined by means of HPLC:

| Sample 1: | 30.3% |
| Sample 2: | 30.5% |
| Sample 3: | 30.7% |

Example 4

35 g of Luwax E (BASF, montan wax, m.p. 75-85° C.) are melted at 140° C. This gives a highly mobile, clear, and colorless melt. 15 g of imidacloprid are then added in portions with stirring.

The hot, golden yellow melt at 140° C. is applied to an aluminum foil, cured, and left to cool. The caramel colored solid is coarsely comminuted, cooled with dry ice, and coarsely ground (Kinematica MB 550, laboratory mixer with beater blade, 8000 rpm).

Yield: 46.93 g

To ascertain the homogeneity, samples were taken from 3 sites and the imidacloprid content was determined by means of HPLC:

|  |  |
|---|---|
| Sample 1: | 30.8% |
| Sample 2: | 30.8% |
| Sample 3: | 30.7% |

Particle sizes measured under the microscope: 100 µm to 300 µm

Example 5

35 g of PEG 35000 (polyethylene glycol) are melted at 140° C. This gives a viscous, clear, and colorless melt, to which 15 g of imidacloprid (Preventol TM) are added in portions with stirring over the course of 30 minutes.

The hot, golden yellow melt at 140° C. is applied to an aluminum foil and left to cool.

This gives a caramel colored solid. This solid is cooled with dry ice and ground (Kinematica MB 550, laboratory mixer with beater blade, 14000 rpm). In order to prevent subsequent caking, mixing takes place with 1% of the fumed silica "Aerosil 200" (based on the solids fraction). This gives 41.49 g of a solid in crumb form.

To ascertain the homogeneity, samples were taken from 3 sites and the imidacloprid content was determined by means of HPLC:

|  |  |
|---|---|
| Sample 1: | 30.3% |
| Sample 2: | 30.6% |
| Sample 3: | 30.6% |

Particle sizes measured under the microscope. 300 µm-500 µm

Example 6

10 g of imidacloprid (Preventol TM) and 40 g of Luwax E (BASF, homopolymeric polyethylene wax, m.p. 75-85° C.) are weighed out into a mixing vessel (Kinematica MB 550, laboratory mixer with beater blade, 14 000 rpm), cooled with dry ice, and mixed with one another. This gives a homogeneous powder.

To test whether shaking causes separation, the powder is introduced into a bottle, shaken on a shaker for 10 minutes, and sampled at three sites in the vessel, the samples being investigated for their imidacloprid fraction by HPLC.

|  |  |
|---|---|
| Sample 1 (top): | 18.3% |
| Sample 2 (middle): | 20.0% |
| Sample 3 (bottom): | 19.1% |

Example 7

10 g of imidacloprid (Preventol TM) and 40 g of Luwax AI3 (BASF, montan wax, m.p. 102-108° C.) are weighed out into a mixing vessel (Kinematica MB 550, laboratory mixer with beater blade, 14 000 rpm), cooled with dry ice, and mixed with one another. This gives a homogeneous powder.

To test whether shaking causes separation, the powder is introduced into a bottle, shaken on a shaker for 10 minutes, and sampled at three sites in the vessel, the samples being investigated for their imidacloprid fraction by HPLC.

|  |  |
|---|---|
| Sample 1 (top): | 19.8% |
| Sample 2 (middle): | 19.6% |
| Sample 3 (bottom): | 19.5% |

Example 8

880 g of imidacloprid (Preventol TM) are added in portions with stirring to a melt, heated to 140° C., of 1320 g of Sasol wax 7040 (Sasol Wax GmbH, paraffin wax CAS No. 8002-74-2; m.p. 68-72° C.). The melt is poured onto aluminum foil and left to solidify. The resulting wax mass is first coarsely comminuted and then placed in a mixing vessel (Kinematica MB 550, laboratory mixer with beater blade, 14 000 rpm), cooled with dry ice, and comminuted. This gives 2137 g of ivory colored wax powder. The particle size, on viewing under the microscope, is about 100 to 200 µm.

To test the homogeneity, samples were taken from 5 sites and were analyzed for their imidacloprid content by HPLC.

Sample 1: 40.0%; sample 2: 39.4%; sample 3: 39.4%; sample 4: 40.2%; sample 5: 40.9%

Example 9

Production of an EPS Block Molding Using Imidacloprid 3.25 g of imidacloprid (Preventol® TM) are metered into 50 kg of EPS granules (Styropor® BF 222) already introduced into the preliminary weighing apparatus of the pre-expander. The charge treated in this way is transferred with stirring into the preliminary expander, after which the EPS granules are subjected to preliminary foaming with steam (105° C.) to a density of 17.7 kg/m$^3$. After cooling in the fluidized bed, the pre-expanded product is stored at room temperature for 24 hours. The resulting material is foamed with steam (130° C.) in block molds to form blocks having a density of 15.05 kg/m$^3$. The condensation water (process water) that is obtained during the pre-expansion and shaping operations contained imidacloprid at a concentration of 1.9 mg/l.

Example 10

Production of an EPS Block Molding Using Inventive Imidacloprid/Wax Mixture 8.13 g of the product obtained in example 8 are metered into 50 kg of EPS granules (Styropor® BF 222) already introduced into the preliminary weighing apparatus of the pre-expander. The charge treated in this way is transferred with stirring into the preliminary expander, after which the EPS granules are subjected to preliminary foaming with steam (105° C.) to a density of 17.7 kg/m$^3$. After cooling in the fluidized bed, the pre-expanded product is stored at room temperature for 24 hours. The resulting material is foamed with steam (130° C.) in block molds to form blocks having a density of 15.05 kg/m$^3$. The condensation water (process water) that is obtained during the pre-expansion and shaping operations contained imidacloprid at a concentration of 1.4 mg/l.

What is claimed is:

1. An insecticidal polymer mixture comprising:
   an expandable polymer comprising a blowing agent,
   an insecticide, and
   a wax, and
   excluding glycerol esters.

2. The mixture as claimed in claim 1, wherein the insecticide is selected from the group consisting of imidachloprid, thiacloprid, thiamethoxam, and mixtures thereof.

3. The mixture as claimed in claim 1 or 2, wherein the expandable polymer is a polystyrene.

4. The mixture as claimed in claim 1 or 2, wherein the wax is at least one wax selected from the group consisting of polyethylene waxes, paraffin waxes, montan waxes, and polyethylene glycol waxes.

5. The mixture as claimed in claim 4, wherein at least one wax has a melting point of 65° C. to 150° C.

6. The mixture as claimed in claim 4, wherein at least one wax has a melting point of 75° C. to 130° C.

7. The mixture as claimed in claim 1, wherein a ratio of insecticide to wax in the mixture is 5:95 to 70:20.

8. An insecticidal polymer particle comprising an expanded polystyrene coated with a mixture comprising:
   at least one wax, and
   at least one insecticide selected from the group consisting of imidachloprid, thiacloprid and thiamethoxam f
   excluding glycerol esters.

9. A method for producing the insecticidal polymer particle as claimed in claim 8, the method comprising:
   mixing the at least one insecticide, the at least one wax, and a polystyrene containing at least one blowing agent mixture; and
   heating the mixture at a temperature greater than or equal to a temperature at which the wax melts to expand the polystyrene and produce the polymer particles coated with the mixture.

10. The method as claimed in claim 9, wherein the temperature is 65° C. to 150° C.

11. The method as claimed in claim 9, wherein the temperature is 75° C. to 130° C.

12. The method as claimed in claim 9 wherein the mixture is heated with superheated steam.

13. A molding comprising the insecticidal polymer particle as claimed in claim 8.

14. A molding comprising the mixture as claimed in claim 1.

15. A building material or insulation material comprising the molding as claimed in claim 13 or 14.

16. An insecticidal polymer mixture comprising:
   an expandable polystyrene comprising a blowing agent,
   an insecticide selected from the group consisting of imidachloprid, thiacloprid and thiamethoxam, and
   a wax, and
   excluding glycerol esters.

17. The mixture as claimed in claim 16, wherein:
   the wax comprises at least one wax selected from the group consisting of A polyethylene waxes, paraffin waxes, montan waxes, and polyethylene glycol waxes, and at least one wax has a melting point of 75° C. to 130° C.; and
   a ratio of insecticide to wax in the mixture is 10:90 to 50:50.

18. The mixture as claimed in claim 17, wherein:
   the mixture comprises 30% to 99% of the polymer, 0.001% to 0.3% of the insecticide, 0.1% to 30% of the wax, no glycerol esters; and
   the at least one wax has a melting point of 100° C. to 120° C.

* * * * *